(12) United States Patent
Wen

(10) Patent No.: US 9,006,683 B2
(45) Date of Patent: Apr. 14, 2015

(54) PORTABLE STERILIZING DEVICE

(71) Applicant: Jing Pin International Industry Co., Ltd., Hsinchu (TW)

(72) Inventor: Chiao Wei Wen, Hsinchu (TW)

(73) Assignee: Jing Pin International Industry Co., Ltd., Hsinchu (TW)

( * ) Notice: Subject to any disclaimer, the term of this patent is extended or adjusted under 35 U.S.C. 154(b) by 22 days.

(21) Appl. No.: 14/079,471

(22) Filed: Nov. 13, 2013

(65) Prior Publication Data
US 2015/0076363 A1      Mar. 19, 2015

(30) Foreign Application Priority Data

Sep. 17, 2013   (TW) .............................. 102217518 U

(51) Int. Cl.
*A61L 2/10* (2006.01)
*A61L 2/08* (2006.01)

(52) U.S. Cl.
CPC ........................................ *A61L 2/10* (2013.01)

(58) Field of Classification Search
USPC ........... 250/372, 455.11, 458.1, 459.1, 461.1, 250/485.1, 492.1, 504 R, 504 H, 5, 26; 215/11.1, 11.6, 13.1, 400; 422/24
See application file for complete search history.

(56) References Cited

U.S. PATENT DOCUMENTS

| | | | |
|---|---|---|---|
| 6,000,565 A | * | 12/1999 | Ibeagwa ....................... 215/11.6 |
| 2010/0044582 A1 | * | 2/2010 | Cooper et al. ........... 250/455.11 |
| 2010/0102252 A1 | * | 4/2010 | Harmon et al. ............ 250/492.1 |
| 2010/0150785 A1 | * | 6/2010 | Woolman et al. ............. 422/116 |
| 2012/0261593 A1 | * | 10/2012 | Noori ......................... 250/492.1 |
| 2014/0356229 A1 | * | 12/2014 | Farren ............................. 422/24 |

* cited by examiner

*Primary Examiner* — Bernard E Souw
(74) *Attorney, Agent, or Firm* — Maschoff Brennan

(57) ABSTRACT

A portable sterilizing device for sterilizing at least one of a feeding bottle, a nipple, a bottle stopper, and a cap comprises: a sterilization covering body and a containing bottle. The sterilization covering body includes a covering member and a sterilizing member provided on the covering member, a UV-light emitting unit of the sterilizing member is emitting the UV light in a covering direction. The containing bottle includes a body portion and a connecting portion extensively formed from the body portion, the body portion covering the covering member along the covering direction in a manner that the connecting portion is attached to the attaching portion so as to form a containing space that faces toward the UV light for the sterilization. Thus, the portable sterilizing device has the advantages of small size and low power consumption, and therefore it is convenient for baby caretaker to portably carry it.

10 Claims, 7 Drawing Sheets

PORTABLE STERILIZING DEVICE

FIELD OF THE INVENTION

The present invention relates to a sterilizing device, and more particularly, to a portable sterilizing device having a containing space for containing a feeding bottle, a nipple, a bottle stopper, and a cap.

BACKGROUND OF THE INVENTION

A baby's immune system is not fully developed until he/she is over 6 months old. For the comfort and the health of a baby, people pay more attention to articles that may be in any contact with a baby. In general, since a baby is feed with milk or breast milk as a daily food, it needs to thoroughly sterilize the baby necessities such as a feeding bottle, a nipple, a bottle stopper, and a cap prior to or after the use to thus prevent the hurt to the baby's health.

There are two conventional methods for sterilization. One of the methods applies a high-temperature steam generated by a sterilization container to sterilize a feeding bottle, a nipple, a bottle stopper, and a cap. The other method is for boiling a nipple for 3-5 minutes and boiling a feeding bottle, a bottle stopper, and a cap for 8-12 minutes with water and thereafter drying the feeding bottle, the nipple, the bottle stopper, and the cap in the air.

However, for a baby caretaker in outdoors, the sterilization container is too bulky to carry it in outdoors and is high power consumption as well. In addition, it is hard to boil water in outdoors, so it is not practicable to apply boiling water for sterilization. Furthermore, the conventional sterilizing methods that apply a high-temperature steam or boiling water may not only likely cause a burn accident but also tend to result in a hazardous substances released from the chemical material deformation of materials such as plastics, rubbers and any other polymers.

SUMMARY OF THE INVENTION

Therefore, in view of the above drawbacks, the present invention provides a portable sterilizing device that is not only for convenient carriage, but also prevents any hazardous substances released from the material of plastics, rubbers and any other polymers.

A portable sterilizing device for sterilizing at least one of a feeding bottle, a nipple, a bottle stopper and a cap, comprising: a sterilization covering body, including a covering member and a sterilizing member provided on the covering member, the sterilizing member including a power supply unit and a UV-light emitting unit, the UV-light emitting unit being electrically connected with the power supply unit and emitting the UV light in a covering direction, the covering member being extensively formed with an attaching portion; and a containing bottle, including a body portion and a connecting portion extensively formed from the body portion, the body portion covering the covering member along the covering direction in a manner that the connecting portion is attached to the attaching portion so as to form a containing space that faces toward the UV light emitted from the UV-light emitting unit for the sterilization.

According to an embodiment of the present invention, the connecting portion includes an extending element and a fastening element, the extending element extends upward from the body portion, the fastening element is formed protruding outward from the extending element, and the attaching portion has a fastening hole corresponding to the fastening element.

According to an embodiment of the present invention, the covering member has a stepped flange at an edge thereof, and the body portion has a complementary stepped flange corresponding to the stepped flange.

According to an embodiment of the present invention, the connecting portion is a threaded portion, and the attaching portion is a complementary threaded portion to the threaded portion.

According to an embodiment of the present invention, the connecting portion is a circular rib portion, and the attaching portion is a circular groove portion complementary to the circular rib portion.

According to an embodiment of the present invention, the sterilizing member further includes a push switch including a cover element and a pressing element, the cover element is placed for covering a the power supply unit by means of providing a pressing gap between the cover element and a power switch of the power supply unit, the pressing element is arranged within the pressing gap for triggering the power switch by means of a pushing operation.

According to an embodiment of the present invention, the covering member is extensively downward formed an annular covering wall, the attaching portion is located on the annular covering wall, and the containing space is sealed by the annular covering wall and the body portion.

According to an embodiment of the present invention, the sterilizing member further includes a timer module electrically connected with the power supply unit.

According to an embodiment of the present invention, a cross sectional area of the containing space is gradually decreased along the height of the body portion from top to bottom.

According to an embodiment of the present invention, a height of the portable sterilizing device is between 250 mm and 350 mm, a length and a width of a cross-sectional area of the connecting section between the covering member and the body portion is between 75 mm and 100 mm, and a length and a width of a bottle bottom of the body portion is between 55 mm and 80 mm.

By technical means applied by the present invention, the portable sterilizing device having a containing space for accommodating a feeding bottle, a nipple, a bottle stopper, and a cap applies the UV light to excite oxygen into ozone to thus remove bacteria and rotten milk odor existing in the feeding bottle, the nipple, the bottle stopper, and the cap that are received in the containing space. In addition, the portable sterilizing device that uses UV light for sterilizing has the advantages of small size and low power consumption, and therefore it is convenient for baby caretaker to portably carry it. Moreover, the sterilization of UV light is advantageous in that it not only avoids a burn accident caused by the high-temperature steam or boiling water, but also prevents the harmful substances being released from the material of plastics, rubbers and other polymers caused by the high-temperature steam or boiling water. Moreover, it further reduces the possibility of chronic poisoning for a baby and a baby caretaker as long-term exposing in front of harmful substances.

BRIEF DESCRIPTION OF THE DRAWINGS

The structure and the technical means adopted by the present invention to achieve the above and other objectives

DETAILED DESCRIPTION OF THE PREFERRED EMBODIMENTS

Embodiments are described in detail below with reference to the FIG. 1 to FIG. 6, and the description is used for explaining the embodiments of the present invention only but not for limiting the scope of the claims.

Figure 1:
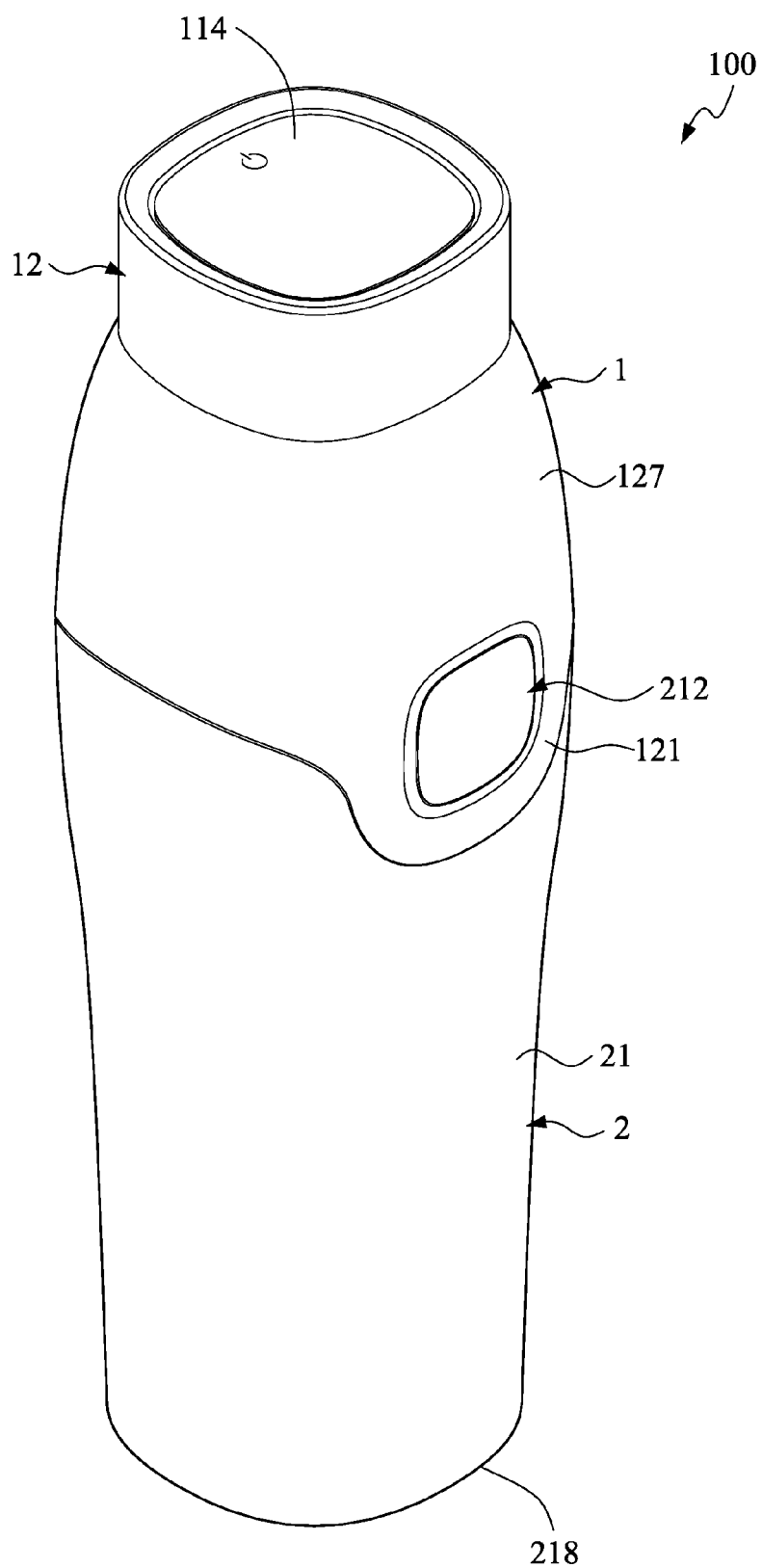
FIG. 1 is a stereogram illustrating a portable sterilizing device according to an embodiment of the present invention.
Figure 2:
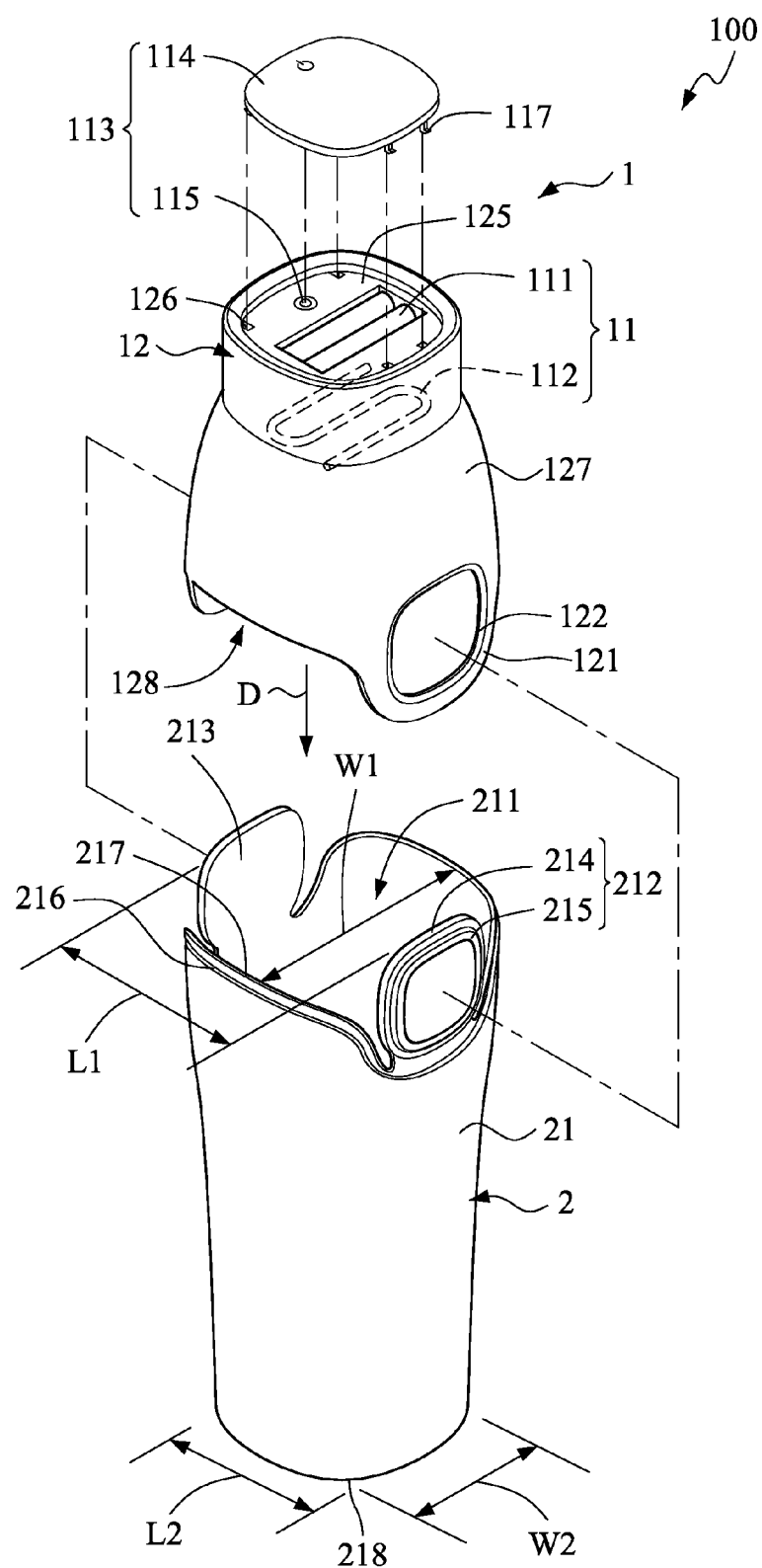
FIG. 2 is an explosion diagram illustrating the portable sterilizing device according to the embodiment of the present invention.
Figure 4:
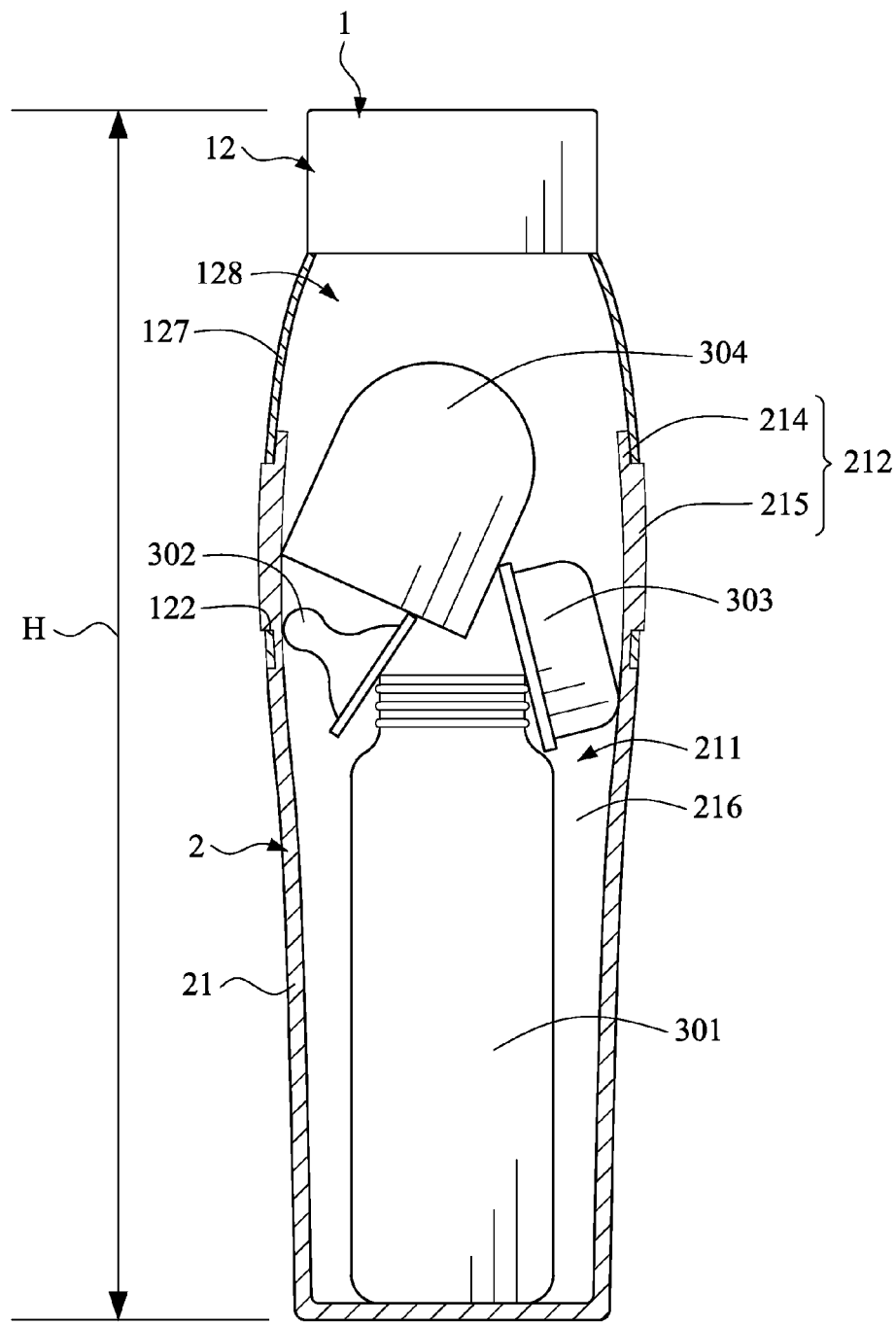
FIG. 4 is a schematic diagram of use illustrating the portable sterilizing device according to the embodiment of the present invention.

As referring to FIG. 1 and FIG. 2, a portable sterilizing device 100 according to one embodiment of the present invention is provided for sterilizing at least one of a feeding bottle 301, a nipple 302, a bottle stopper 303, and a cap 304, as shown in FIG. 4. The portable sterilizing device 100 includes a sterilization covering body 1 and a containing bottle 2.

The sterilization covering body 1 includes a sterilizing member 11 and a covering member 12. The sterilizing member 11 is supplied on the covering member 12 and includes a power supply unit 111 and a UV-light emitting unit 112. The UV-light emitting unit 112 is electrically connected with the power supply unit 111 and projects UV light toward a covering direction D. An attaching portion 121 is formed by extending the covering member 12. Specifically, the power supply unit 111 may be a battery chamber. The containing bottle 2 includes a body portion 21. The body portion 21 is covered by the covering member 1 along the covering direction D, and thus a sealed containing space 211 is formed by covering the body portion 21 with the covering member 1. More particularly, the body portion 21 is extendingly formed with a connecting portion 212. The connecting portion 212 is formed within the covering member 12 and the body portion 21 as the attaching portion 121 and the containing space 211 are connected with each other. A placing opening 213 of the containing space 211 faces toward the UV light projecting from the UV-light emitting unit 112 to thus apply the UV-light emitting unit 112 to sterilize the area in the containing space 211. As referring to FIG. 2 to FIG. 4, the UV-light emitting unit 112 receives an electrical energy of the power supply unit 111 and emits in the covering direction D to project the UV light, and thus oxygen in the containing space 211 is excited to produce ozone to fulfill the containing space 211 with ozone. Ozone is able to sterilize bacteria, viruses, mildew and other unicellular microbe to be immediate dead or reproductive capacity losing, and therefore it able to effectively kill the bacteria and remove rotten milk odor in the feeding bottle 301, the nipple 302, the bottle stopper 303, and the cap 304. In addition, the covering member 12 is preferably made from material that is able to filter the UV light. In this embodiment, the covering member 12 is made from material of polypropylene able to filter the UV light, and thus it is able to avoid the eye damage from the UV light. However, the present invention is not limited to this. The covering member 12 may be made from any material that is unable to filter the UV light.

As referring to FIG. 1, FIG. 2, and FIG. 4, in the embodiment of the present invention, the connecting portion 212 includes an extending element 214 and a fastening element 215. The extending element 214 is upwardly (i.e. along a height direction of the body portion 21) extended from the body portion 21. The fastening element 215 is an outward convex extending from the extending element 214, and the attaching portion 121 is supplied with a fastening hole 22 corresponding to the fastening element 215. As a result, the fastening hole 122 is buckled with the fastening element 215 to connect the covering member 12 with the body portion 21, and thus the containing space 211 is sealed by the covering member 12 and the body portion 21.

Figure 5:
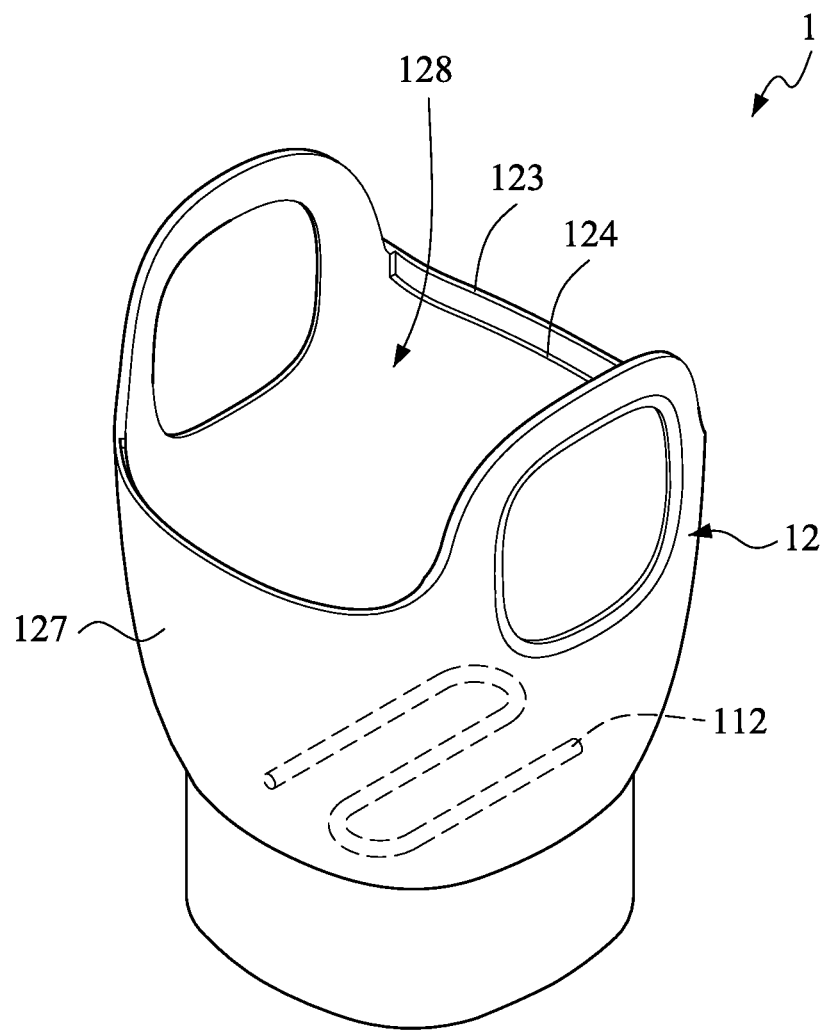
FIG. 5 is a stereogram illustrating the sterilizing covering body of the portable sterilizing device according to the embodiment of the present invention.

As referring to FIG. 2 and FIG. 5, optionally, an edge 123 of the covering member 12 has a stepped flange 124, and a fastening hole 216 of the body portion 21 has an annular covering wall 217 corresponding to the stepped flange 124. The annular covering wall 217 is correspondingly engaged with the stepped flange 124 to closely seal the sterilization covering body 1 and the containing bottle 2. However, the present invention is not limited to this. The stepped flange 124 of the covering member 12 can be formed as a concave toward outside, and the annular covering wall 217 of the body portion 21 can also be formed as a convex toward outside.

Figure 3:
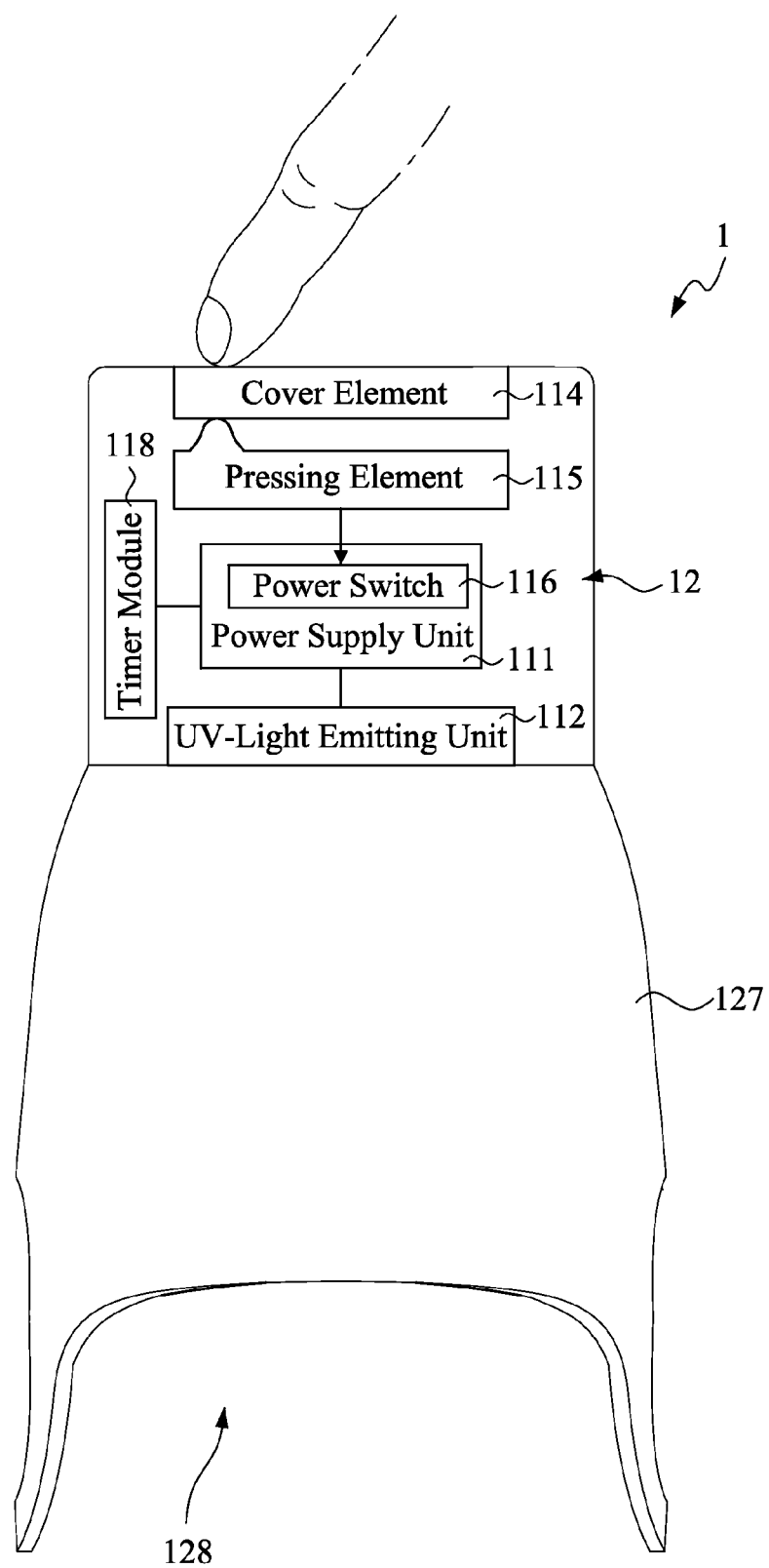
FIG. 3 is a block diagram illustrating a sterilization covering body of the portable sterilizing device according to the embodiment of the present invention.

As referring to FIG. 1 to FIG. 3, in the embodiment of the present invention, the sterilizing member 11 further provides with a push switch 113. The push switch 113 includes a cover element 114 and a pressing element 115. The cover element 114 is covered on an upper surface 125 of the covering member 12 so as to cover the power supply unit 111. A press gap is formed between the cover element 114 and a power switch 116 of the power supply unit 111, and the pressing element 115 is provided between the cover element 114 and the press gap of the power supply unit 111, and thus the power switch 116 is triggered by pressing. Particularly, in the embodiment, the cover element 114 is provided with several fastening element 117 fastened on several fastening hole 126 of the covering member 12. When a user presses the cover element 114 corresponding to the position of the pressing element 115, the pressing element 115 will trigger the power switch 116 to enable the power supply unit 111 to transmit the electrical energy to the UV-light emitting unit 112.

As referring to FIG. 2 to FIG. 4, in the embodiment of the present invention, the covering member 12 is extending downwardly to form an annular covering wall 127. A covering space is formed and is surrounded by the annular covering wall 127, and the attaching portion 121 is provided on the annular covering wall 127. In detail, by attaching the attaching portion 121 with the connecting portion 212, the containing space 211 is sealed by the annular covering wall 127 and the body portion 21 to form a large space together with the covering space 128. It is noted that the covering member 12 may not provided with the annular covering wall 127 and the covering space 128, and the covering member 12 is connected with the body portion 21 by attaching the attaching portion 121 with the connecting portion 212.

As referring to FIG. 3, in the embodiment of the present invention, the sterilizing member 11 further includes a timer module 118 electrically connected with the power supply unit 111. Thereby, after the UV-light emitting unit 112 projects UV light for a predetermined time period, the power supply unit 111 will stop the transmission of the electric energy to the UV-light emitting unit 112. In the present embodiment, the predetermined time period is 6 minutes. However, the present invention is not limited to this. The predetermined time period may be configured as larger or smaller than six minutes.

As referring to FIG. 1, FIG. 2, and FIG. 4, in the embodiment of the present invention, a cross sectional area of the containing space 211 is gradually reduced toward downward from a connecting portion between the covering member 12 and the body portion 21. In detail, the nipple 302, the bottle stopper 303, and the cap 304 will be maintained in a position of the containing space 211 adjacent to the UV-light emitting unit 112, such as in the covering space 128, when they are putted into the containing space 211 while the feeding bottle 301 is already in the containing space 211. Thus, it will ensure the feeding bottle 301, the nipple 302, the bottle stopper 303, and the cap 304 to be not blocked by the feeding bottle 301 in front of the UV light, so a sterilization effect will be enhanced. Preferably, a height H of the portable sterilizing device 100 is between 250 mm and 350 mm, and a length L1 and a width W1 of the cross sectional area of the connecting portion between the covering member 12 and the body portion 21 is between 75 mm and 100 mm, and a length L2 and a width W2 of a bottle bottom 218 of the body portion 21 is between 55 mm and 80 mm.

Figure 6:
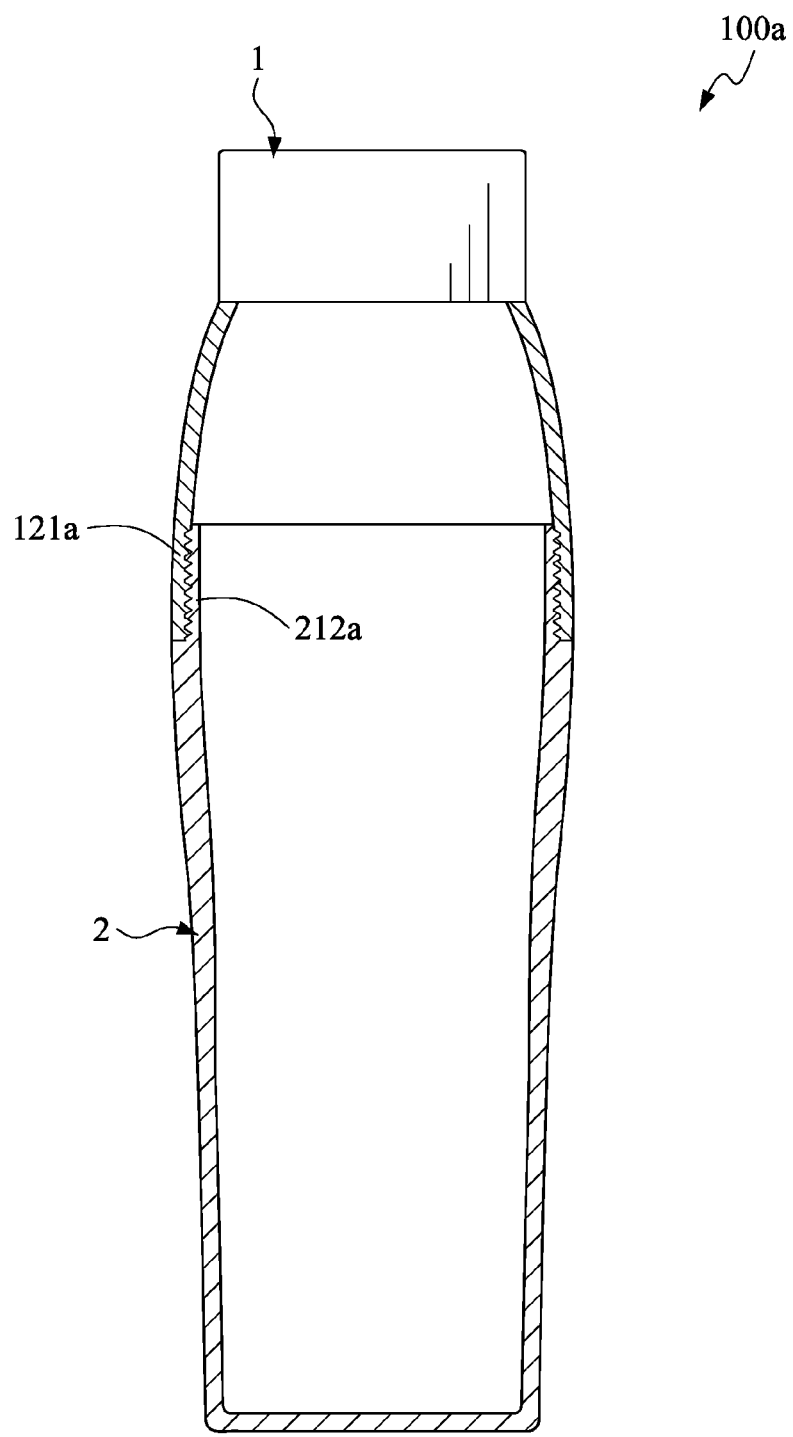
FIG. 6 is a perspective drawing illustrating a portable sterilizing device according to another embodiment of the present invention.

As referring to FIG. 6, a portable sterilizing device 100a according to another embodiment of the present invention is similar to the portable sterilizing device 100 of FIG. 1 to FIG. 5, and thus the same parts of the embodiment will not be repeated here. The difference is that the connecting portion 212a is a screw threaded portion, and the attaching portion 121a is a threaded portion matching with the screw threaded portion. The attaching portion 121a is screwed into the connecting portion 212a to seal the containing space 211 by connecting the covering member 12 and the body portion 21.

Figure 7:
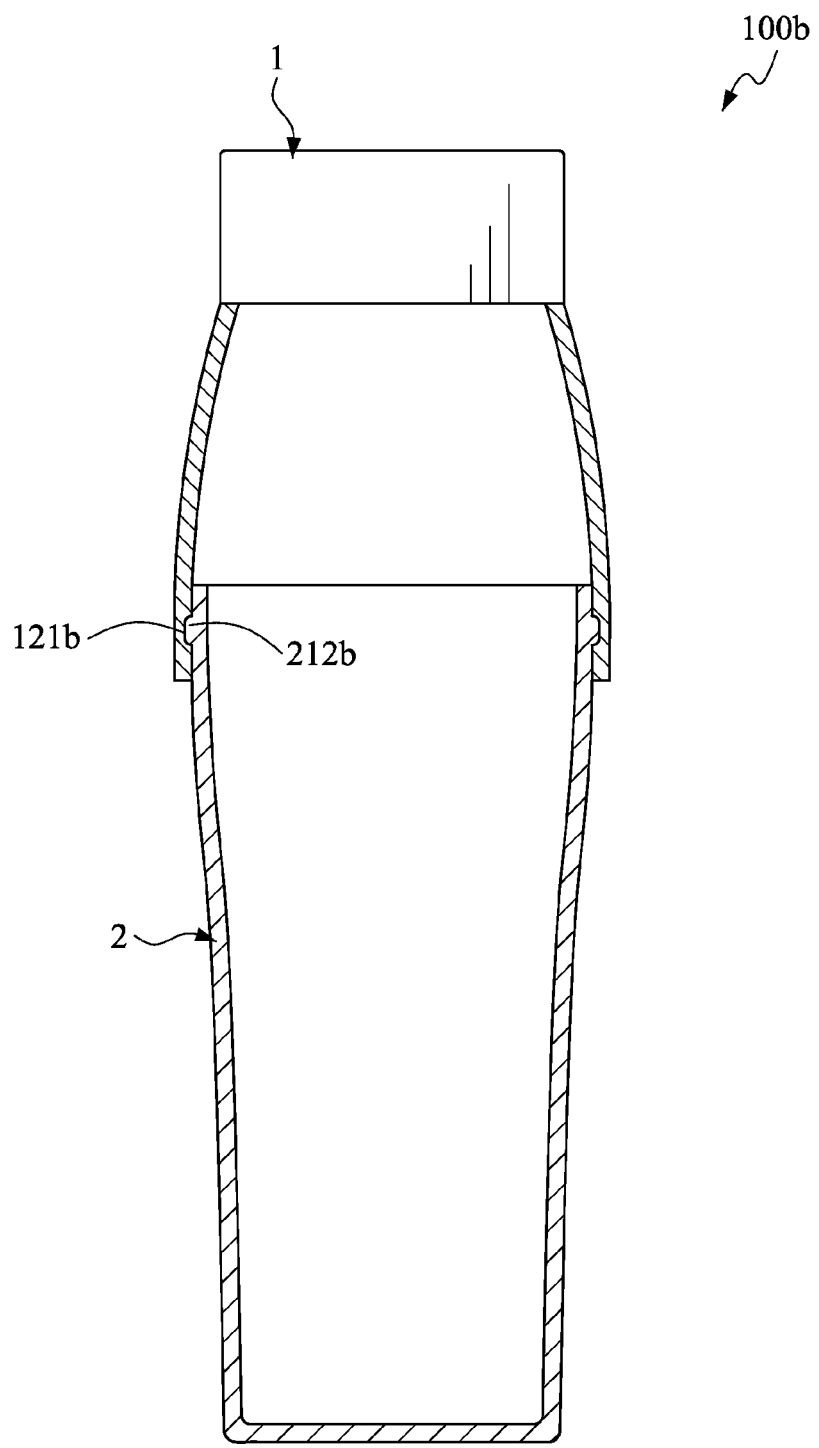
FIG. 7 is a perspective drawing illustrating a portable sterilizing device according to another embodiment of the present invention.

Alternatively, as referring to FIG. 7, a connecting portion 212b of a portable sterilizing device 100b according to another embodiment of the present invention is a circular rib portion, and an attaching portion 121b is a groove portion matching with the circular rib portion. The attaching portion 121b is engaged with the connecting portion 212b to seal the containing space 211 by means of the covering member 12 and the body portion 21. However, the present invention is not limited to this, and the connecting portion and the attaching portion can be connecting with each other in other manners.

The above description should be considered as only the discussion of the preferred embodiments of the present invention. However, a person skilled in the art may make various modifications to the present invention. Those modifications still fall within the spirit and scope defined by the appended claims.

What is claimed is:

1. A portable sterilizing device for sterilizing at least one of a feeding bottle, a nipple, a bottle stopper and a cap, comprising:
a sterilization covering body, including a covering member and a sterilizing member provided on the covering member, the sterilizing member including a power supply unit and a UV-light emitting unit, the UV-light emitting unit being electrically connected with the power supply unit and emitting the UV light in a covering direction, the covering member being extensively formed with an attaching portion; and
a containing bottle, including a body portion and a connecting portion extensively formed from the body portion, the body portion covering the covering member along the covering direction in a manner that the connecting portion is attached to the attaching portion so as to form a containing space that faces toward the UV light emitted from the UV-light emitting unit for the sterilization.

2. The portable sterilizing device as claimed in claim 1, wherein the connecting portion includes an extending element and a fastening element, the extending element extends upward from the body portion, the fastening element is formed protruding outward from the extending element, and the attaching portion has a fastening hole corresponding to the fastening element.

3. The portable sterilizing device as claimed in claim 1, wherein the covering member has a stepped flange at an edge thereof, and the body portion has a complementary stepped flange corresponding to the stepped flange.

4. The portable sterilizing device as claimed in claim 1, wherein the connecting portion is a threaded portion, and the attaching portion is a complementary threaded portion to the threaded portion.

5. The portable sterilizing device as claimed in claim 1, wherein the connecting portion is a circular rib portion, and the attaching portion is a circular groove portion complementary to the circular rib portion.

6. The portable sterilizing device as claimed in claim 1, wherein the sterilizing member further includes a push switch including a cover element and a pressing element, the cover element is placed for covering a the power supply unit by means of providing a pressing gap between the cover element and a power switch of the power supply unit, the pressing element is arranged within the pressing gap for triggering the power switch by means of a pushing operation.

7. The portable sterilizing device as claimed in claim 1, wherein the covering member is extensively downward formed an annular covering wall, the attaching portion is located on the annular covering wall, and the containing space is sealed by the annular covering wall and the body portion.

8. The portable sterilizing device as claimed in claim 1, wherein the sterilizing member further includes a timer module electrically connected with the power supply unit.

9. The portable sterilizing device as claimed in claim 1, wherein a cross sectional area of the containing space is gradually decreased along the height of the body portion from top to bottom.

10. The portable sterilizing device as claimed in claim 1, wherein a height of the portable sterilizing device is between 250 mm and 350 mm, a length and a width of a cross-sectional area of the connecting section between the covering member and the body portion is between 75 mm and 100 mm, and a length and a width of a bottle bottom of the body portion is between 55 mm and 80 mm.

* * * * *